United States Patent [19]

Beard, Jr. et al.

[11] 4,307,261

[45] Dec. 22, 1981

[54] PROCESS FOR SEPARATING FERRIC IRON FROM CHLORINATED HYDROCARBONS

[75] Inventors: William Q. Beard, Jr.; Richard L. Wilson, both of Wichita, Kans.

[73] Assignee: Vulcan Materials Company, Wichita, Kans.

[21] Appl. No.: 122,040

[22] Filed: Feb. 19, 1980

[51] Int. Cl.$^3$ ............................................. C07C 17/38
[52] U.S. Cl. ................................................... 570/262
[58] Field of Search ........................... 260/652 P, 663; 570/262, 250

[56] References Cited

U.S. PATENT DOCUMENTS

| | | | |
|---|---|---|---|
| 3,265,748 | 8/1966 | Hurt | 260/663 |
| 3,420,749 | 1/1969 | Dehn | 260/652 P |
| 3,654,093 | 4/1972 | Schexnader et al. | 260/652 P |

OTHER PUBLICATIONS

Kovacic and Volz, JACS 81, 3261-3263, (1959).

*Primary Examiner*—Delbert E. Gantz
*Assistant Examiner*—Joseph A. Boska
*Attorney, Agent, or Firm*—Burns, Doane, Swecker & Mathis

[57] ABSTRACT

Ferric iron is removed from chlorinated hydrocarbons having less than 6 carbon atoms per molecule by intimately contacting the latter with an oil that comprises one or more hydrocarbons having at least 6 carbon atoms per molecule. The hydrocarbon oil is present in an amount sufficient to interact with a major portion of the ferric iron. The resulting mixture of the chlorinated hydrocarbon stream and the hydrocarbon oil is heated simultaneously with the intimate contacting, and a precipitate is allowed to form. The chlorinated hydrocarbon stream is then separated from the hydrocarbon oil and from the precipitate, and the precipitate is subsequently separated from the hydrocarbon oil.

2 Claims, No Drawings

PROCESS FOR SEPARATING FERRIC IRON FROM CHLORINATED HYDROCARBONS

BACKGROUND

1. Field of the Invention

Valuable chlorinated hydrocarbons such as ethyl chloride, 1,1-dichloroethane, methylchloroform, and analogous chlorinated derivatives of higher hydrocarbons such as propane or butane are commonly made by liquid phase catalytic hydrochlorination of the corresponding unsaturated precursor such as ethylene, vinyl chloride or vinylidene chloride. Ferric chloride is usually used as the catalyst in such processes. However, the separation of ferric iron from chlorinated hydrocarbons has been a long-standing problem. The presence of ferric iron, particularly in the form of ferric chloride catalyst, during the flashing and recovery of the desired chlorinated hydrocarbons causes dehydrochlorination of the chlorinated hydrocarbons such as methylchloroform and subsequent polymerization of the resulting unsaturated product. Many methods have been tried for removal, deactivation and/or disposal of ferric chloride, but all have serious deficiencies.

2. State of the Art

The most obvious method of removing ferric chloride from chlorinated hydrocarbon streams is the extraction of the ferric chloride with aqueous acid solutions. The ferric chloride is unexpectedly difficult to remove in this manner. Part of the ferric chloride apparently retains some solubility in the organic layer by forming complexes with polymeric material. Furthermore, the resulting chlorinated hydrocarbon product must be dried, which is an expensive procedure on an industrial scale.

Ferric chloride has also been separated from methylchloroform by using almost anhydrous bases, such as the hydroxides of sodium, potassium, and calcium, to absorb the ferric chloride. These materials are relatively inefficient and allow easy pluggage of absorption equipment by the ferric hydroxide produced. The spent bases would constitute a difficult disposal problem. Such a separation process is described in Japanese Pat. No. 71 16,491.

German Pat. No. 1,235,878 discloses a process in which ammonia is used to precipitate ferric chloride. The ammonia is thereafter separated from the chlorinated hydrocarbon product by distillation. Ammonia has also been used in conjunction with steam to precipitate the ferric chloride while removing the chlorinated hydrocarbons by steam distillation (see U.S. Pat. No. 3,115,528). However, the use of these ammonia methods can introduce small amounts of amines as contaminants into the product. Amines or excess ammonia would be at least as undesirable as water. Moreover, steam distillation can aggravate the hydrolysis of a chlorocarbon such as methylchloroform, which is known to occur with great facility in the presence of ferric chloride and moisture.

Ferric chloride has also been removed from chlorinated hydrocarbons by sequestration of the ferric iron by a lower alkanol solution of a partial amide of ethylenediaminetetraacetic acid. Such a process is taught in U.S. Pat. No. 3,848,005. However, this process was intended primarily for the deactivation of small amounts of iron during distillation and thus would not be economical or practical for removal of the relatively large amounts of hydrochlorination catalyst.

Ferric chloride has also been removed from chlorinated hydrocarbons by contacting the chlorinated hydrocarbon streams with activated charcoal and with other porous adsorbents such as silica gel, alumina, or molecular sieves. See, for example, British Pat. No. 1,380,497 and Japanese Pat. No. 72 16,801. The adsorbents, particularly activated carbon, work well in removing the iron chloride but contain water which is released to the chlorinated hydrocarbon with the concomitant undesirable effects. Moreover, regeneration of these adsorbents presents problems in corrosion and disposal, since the adsorbed iron has to be removed with an aqueous acid.

The removal of ferric chloride from chlorinated solvents has also been attempted by reduction of the ferric chloride to ferrous chloride through treatment with reducing agents such as stannous chloride, cuprous chloride, or iron, followed by distillation of the solvent, as described in U.S.S.R. Pat. No. 530,877. The use of stannous chloride or cuprous chloride presents an increased expense, and the use of iron creates an increase in the amount of ferrous chloride requiring disposal.

In U.S. Pat. No. 4,001,345 the use of quaternary ammonium salts has been proposed to inhibit the catalytic effects of ferric chloride on methylchloroform during distillation. However, because quaternary ammonium compounds are expensive, the operational cost of such a process would be high. In addition, decomposition of the quaternary ammonium salts to amines may take place.

Experience has shown that the disposal of ferric chloride-containing material from hydrochlorination processes poses a constant series of problems in commercial practice. A considerable amount of chlorinated hydrocarbon remains with the ferric chloride-containing material after conventional separation, making it highly corrosive. In addition, flasher fouling has caused a considerable amount of shut-down time. Moreover, increasingly stringent regulations for the disposal of hazardous landfill material have caused an increased impetus to find a more acceptable method for removing and disposing of ferric iron in hydrochlorination processes.

Thus, it is an object of the present invention to provide a process for the removal of ferric iron from hydrochlorination processes whereby the removal of ferric iron is accomplished without substantial decomposition of the chlorinated hydrocarbon product.

It is also an object of the present invention to provide a process for the removal of ferric iron from hydrochlorination processes in which fouling of the hydrochlorination apparatus is substantially reduced.

It is also an object of the present invention to provide a process for the removal of ferric iron from chlorinated hydrocarbons wherein no moisture is introduced into the system.

It is another object of the present invention to provide a low-cost process for the removal of ferric iron from chlorinated hydrocarbons, using a relatively high-boiling hydrocarbon oil as a medium in which dissolved ferric chloride is converted into a filtrable, granular precipitate.

It is still another object of the present invention to provide a process for the removal of ferric iron from hydrochlorination processes whereby the handling properties of the residues are improved.

It is a further object of the present invention to provide a process for the removal of ferric iron from hydrochlorination processes whereby the iron-containing residues are rendered non-hazardous in order to allow ordinary landfill disposal in compliance with environmental protection laws and regulations.

These and other objects, as well as the use of the invention in attaining them, will become more fully apparent from the description which follows.

SUMMARY OF THE INVENTION

The present invention provides a process for the removal of ferric iron from relatively volatile chlorinated hydrocarbons containing 1 to 5 carbon atoms per molecule. According to the invention, a $C_1$ to $C_5$ chlorinated hydrocarbon or a mixture thereof containing ferric iron is intimately contacted in liquid phase with a relatively less volatile hydrocarbon or chlorinated hydrocarbon oil which comprises hydrocarbons or chlorinated hydrocarbons containing at least 6 carbon atoms per molecule and having a boiling point or range at least 20° C. higher than the boiling point or range of the chlorinated hydrocarbons being treated. The less volatile oil is present in an amount sufficient to interact with a major portion of the ferric iron contained in the chlorinated hydrocarbon being treated. The resulting intimate mixture of the iron-containing chlorinated hydrocarbon and the less volatile oil is heated until a solid precipitate is formed. The volatile chlorinated hydrocarbon is then separated from the less volatile oil, for instance, by flashing or fractional distillation, and the precipitate is subsequently mechanically separated from the oil.

DETAILED DESCRIPTION OF THE INVENTION

According to the present invention, dissolved or partially dissolved ferric iron compounds, such as ferric chloride, are removed from low-boiling chlorinated hydrocarbons with virtually no decomposition of the latter. This removal is accomplished by contacting the iron-contaminated chlorinated hydrocarbons in liquid phase with a hot, relatively high-boiling oil composition comprising one or more hydrocarbons or partially chlorinated hydrocarbons or a mixture thereof. As a result, the oil chemically reduces the ferric compound to the ferrous state and thus forms a solid precipitate of iron compounds combined with a small amount of carbonaceous material that is substantially insoluble in the liquids present. Unlike conventionally separated ferric chloride catalyst residues, which tend to be deliquescent and corrosive, the precipitate obtained according to this invention is an easily filtered, granular, dark-colored solid that is non-hazardous for landfill disposal. Any adherent liquid oil can be readily removed from the precipitate by washing with a suitable solvent such as a light liquid hydrocarbon or chlorinated hydrocarbon prior to disposal, if desired. It is preferred to use for this purpose the same low-boiling chlorinated hydrocarbon as is used in the principal contacting step in order to permit recycling the wash liquid into the contacting step. Residual chlorinated hydrocarbon or wash liquid can be removed by heating.

The invention may be used in conjunction with any conventional hydrochlorination process which yields as a product a chlorinated hydrocarbon having less than about six carbon atoms per molecule. Such conventional hydrochlorination processes are well known in the art and need not be discussed in detail here. Typically, such processes involve the reaction of hydrogen chloride with an ethylenically-unsaturated $C_2$ to $C_5$ hydrocarbon or chlorocarbon, e.g., ethylene, propylene, pentene, vinyl chloride, vinylidene chloride, allyl chloride, 2-chloropropene, 3-chloro-1-butene, or 5-chloro-2-pentene, or with a mixture of two or more such compounds, in the presence of a ferric chloride ($FeCl_3$) catalyst. Accordingly, the product of such a hydrochlorination reaction is a saturated aliphatic chlorocarbon containing 2 to 5 carbon atoms and 1 to 3 chlorine atoms per molecule or a mixture containing two or more such compounds. The hydrochlorination reaction is ordinarily conducted in liquid phase.

Although other Friedel-Crafts catalysts, such as aluminum chloride and zinc chloride, may be used in typical hydrochlorination processes, such catalysts are not included within the scope of the present invention. When removed from chlorinated hydrocarbons by the process of the present invention, aluminum chloride and zinc chloride would remain hygroscopic, corrosive, and chemically reactive after separation. Ferric halide is therefore unique. Being multivalent, it is chemically reduced by the oil to produce essentially an inert, harmless, easily disposble solid.

In its preferred embodiment, the invention is directed particularly toward the removal of ferric iron from the hydrochlorination reactor product obtained in the manufacture of methylchloroform. In such a process, a chlorocarbon mixture comprising primarily vinyl chloride together with some vinylidene chloride is hydrochlorinated to 1,1-dichloroethane and 1,1,1-trichloroethane (methylchloroform), respectively. Of course, the invention is also applicable when an individual compound such as only vinyl chloride or only vinylidene chloride is hydrochlorinated.

The chlorinated hydrocarbon which is contacted with hot oil according to the present invention comprises the liquid product stream from a typical hydrochlorination process. This chlorinated hydrocarbon product typically contains ferric iron, e.g., ferric chloride ($FeCl_3$), either dissolved therein or suspended therein as a finely divided solid or it may be present both in solution and in suspension. Depending on the nature of the feed to and the conversion in the hydrochlorination reaction, this chlorinated hydrocarbon comprises either one or a plurality of $C_1$ to $C_5$ chlorinated hydrocarbons. According to a preferred embodiment, the iron-contaminated chlorinated hydrocarbon to be treated comprises a mixture of 1,1-dichloroethane and 1,1,1,-trichloroethane (methylchloroform).

The iron-contaminated chlorinated hydrocarbon liquid is contacted with a hydrocarbon oil or partially chlorinated hydrocarbon oil that has a boiling range substantially higher than the boiling point or range of the chlorinated hydrocarbon liquid. The oil may comprise one or more hydrocarbons having at least six carbon atoms, e.g., $C_6$ to $C_{40}$ or higher hydrocarbons. Oil compositions containing an average of at least 12 and up to 40 carbon atoms per molecule have produced excellent results to date. The hydrocarbons may comprise alkanes, alkenes, alkyl benzenes, alkyl naphthalenes, cycloalkanes, cycloalkenes or the like, or mixtures of two or more of such hydrocarbons or kinds of hydrocarbons. When alkylated aromatics are used as the reducing oil, it is preferred to use oil compositions comprising a major or at least a substantial proportion of aromatic compounds having at least one aliphatic side chain containing six or more carbon atoms, e.g., n-hexyl benzene, nonylnaphthalene, etc. Cycloalkenes such as cyclohexene or cyclooctene are also effective in reacting with the ferric iron. Partially chlorinated derivatives of the hydrocarbons listed above and mixtures of the foregoing, especially the mono, di-, tri- or tetrachlorinated derivatives, are similarly useful, although they will usually be economically less attractive unless they happen to be available as a waste stream from a process.

Examples of commercially available hydrocarbon oils which are suitable for the purposes of this invention include Sontex-55NF (Marathon Morco), Soltrol-220 (Phillips Petroleum), Peneteck (Penreco), Nalkylene-500 (Conoco), USP Mineral Oil (Squibb), and n-dodecane (Phillips Petroleum). Other commercial white mineral oil products are also suitable. Hydrocarbon oil compositions composed predominantly of saturated aliphatic hydrocarbons are currently thought to be preferred. Specifications of suitable oil compositions tested are shown in Table I.

TABLE I

| | Specifications of Mineral Oils Tested | | | | |
|---|---|---|---|---|---|
| | n-Dodecane | USP Min. Oil | Sontex-55NF | Soltrol-220 | Peneteck |
| Source | Phillips | Squibb | Marathon Marco | Phillips | Penreco |
| Boiling range (°F.) | 417 | — | — | 460–495 | 516 |
| Viscosity (SUS @ 100° F.) | $a$ | $178^b$ | 55 | 38.5 | 38–42 |
| Flash point (°F.) | 165 | — | 325 | 229 | 265 |
| Specific gravity 60/60° F. | 0.751 | 0.882 | 0.840 | 0.810 | 0.804–0.816 |
| Pour point (°F.) | — | — | +10 | — | +35 |
| Avg. molecular weight | 170 | $390^c$ | 283 | 198 | 212 |
| Percent paraffins | 100 | — | 65.5 | — | — |
| Percent naphthenes$^d$ | 0 | — | 34.5 | — | — |
| Avg. carbon no. | $C_{12}$ | $C_{29}{}^c$ | $C_{20}$ | $C_{14}$ | $C_{15}$ |

$^a$1.257 centipoise at 23.3° C.
$^b$USP minimum specification
$^c$Estimate for white mineral oils based on viscosity and specific gravity
$^d$Naphthenes - saturated cyclic hydrocarbons The exact nature of the chemical reaction between the oil and the ferric salt is not definitely known, and the present invention is not necessarily predicated on any particular reaction mechanism. However, possible mechanisms may be similar to those discussed by Kovacic et al in J. Am. Chem. Soc., 81, 3261 (1959) and in J. Org. Chem. 28, 2551 (1963).

According to the present invention, a chlorinated hydrocarbon product containing ferric iron and comprising one or more relatively low-boiling chlorinated hydrocarbons is intimately contacted or mixed with a relatively higher boiling oil, as defined above. The oil is present in an amount at least sufficient to interact with a major portion of the ferric iron, e.g., sufficient to reduce at least 60% and preferably at least 95% of the iron present to the divalent state. Any proportion of oil to iron-containing chlorinated hyrocarbon can be used with good results as long as the volume of oil is sufficient to provide for intimate contact with the iron halide that is dispersed and/or dissolved in the chlorocarbon, but only a very small amount of the oil is actually required to effect the desired chemical reaction and cause the desired precipitate to form.

Typically, for instance, the chlorocarbon to be treated may contain from 0.01 to 3% ferric chloride catalyst by weight, although compositions containing lower or higher concentrations of ferric halide catalyst may be treated in accordance with this invention. Conveniently, the ratio of oil to chlorocarbon in the contacting zone is maintained between about 10 and about 10,000 volumes of oil per 100 volumes of iron-containing chlorocarbon, preferably between about 30 to about 500 volumes of oil per 100 volumes of the chlorocarbon. Of course, it should be understood that, for instance, when the treatment is conducted in a flash pot, a given batch of the oil may remain in the pot almost indefinitely while the iron-containing chlorocarbon composition is fed into it on a continuous basis and the volatile chlorocarbon is flashed off almost instantaneously and withdrawn from the pot. In such a case, the volume of oil used in the process relative to the volume of chlorocarbon treated in the process over an extended time is almost nil.

The resulting mixture of the chlorinated hydrocarbon and the hydrocarbon oil is heated while maintaining intimate contact between the chlorinated hydrocarbon and the oil. In order to ensure interaction of the ferric iron and the hydrocarbon oil, the mixture is heated to a temperature of at least 30° C. Such heating may be under reflux or under pressure to prevent the escape of the relatively volatile product, or the product may be simultaneously distilled off. The mixture is preferably heated to a temperature of between about 60° and 140° C., and, more preferably, to a temperature of between about 100° and 130° C. In the most preferred embodiment of the invention, the mixture is heated to a temperature of between about 110° and 120° C.

The optimum temperature and residence time of the thermal treatment of course depends to some extent on the chemical characteristics of the particular reducing oil used, the concentration of ferric iron present in the chlorinated hydrocarbon and the proportion of oil to the chlorinated hydrocarbon, but optimum conditions can be readily and routinely determined for any given case by preliminary empirical tests.

While the chlorinated hydrocarbon and the oil are contacted and heated, a precipitate is formed. This precipitate forms as the result of the interaction between the ferric iron and the hot oil. Although the exact nature of this interaction is presently unknown, it has been found that this essentially insoluble precipitate is a composition in which the iron is present predominantly in the divalent state, e.g., as $FeCl_2$, combined either chemically or physically with a small amount of carbonaceous material from the high-boiling oil. The precipitate forms as an easily filtered, dark-colored solid. It is neither hygroscopic nor corrosive, and is therefore nonhazardous for landfill disposal. Such characteristics are distinctly advantageous in light of the concern for the protection of the environment from hazardous wastes. Note, for instance, the Resource Conservation and Recovery Act. "Spent catalyst from hydrochlorinator reactor in the production of 1,1,1-trichloroethane" has been specifically listed in 44 Federal Register 49403, Aug. 22, 1979, Section 250.14(b)(2), as a possible source of hazardous waste.

During the formation of the precipitate, there is no build-up of impurities from the interaction of the hot oil with the ferric iron. The interaction apparently proceeds to the point where all contaminants become part of the precipitate. Thus, a batch of oil may last almost indefinitely, until it is all converted to precipitate, although of course a sufficient volume of liquid oil must be present in the contacting zone, e.g., a flash pot, to provide for contact with the iron-containing chlorocarbon that is fed into the zone either batchwise or continuously and flashed off. There is no indication that the chlorinated hydrocarbon product stream contributes to the precipitate under normal circumstances.

As or after the precipitate has formed, the low-boiling chlorinated hydrocarbon stream is separated from the higher boiling oil and solid precipitate. This can be accomplished by ordinary distillation or more conveniently by flash distillation either in the original treating zone or after transfer to a separate distillation tower, batchwise or continuously, or in any other suitable manner. The residue containing the oil and precipitate can be mechanically separated in any suitable manner, such as filtration or centrifugation. The separation may be accomplished either continuously or periodically. Following separation the precipitate can be washed in order to remove any adsorbed oil, preferably with a portion of the low-boiling chlorinated hydrocarbon that has been recovered from the separation step. Following such a washing step, the recovered chlorinated hydrocarbon wash liquid can be recycled to the contacting step. Alternatively, any other non-noxious wash solvent such as petroleum naphtha may be used and the resulting wash liquid disposed of in whatever manner may be convenient at the particular location and in the particular circumstances.

When the process of the present invention is practiced as described herein, the percentage dehydrochlorination of the chlorinated hydrocarbon product is too small to measure conveniently. That is, ferric iron is removed from chlorinated hydrocarbon streams without any significant decomposition of the chlorinated hydrocarbon product. Furthermore, no noticeable tarry or polymeric decomposition products of the chlorinated hydrocarbon are formed, as shown by the powdery character of the solid precipitate and its ease of separation from the oil. The weight of precipitate obtained is usually of the same order as the weight of ferric chloride initially present, and the consumption of oil is virtually inconsequential. The dried precipitate contains no volatile solvent, is not corrosive, is not hygroscopic, and is, therefore, easily handled. An additional advantage is that no moisture is introduced so that no subsequent solvent-drying step is required.

A preferred embodiment of the present invention comprises continuously feeding a liquid chlorinated hydrocarbon stream containing ferric chloride catalyst from a hydrochlorination reaction to a flash distillation pot which contains a relatively high-boiling hydrocarbon oil that is held at sufficiently high temperature to distill off the chlorinated hydrocarbon and to achieve rapid reaction of the ferric chloride with the oil as the chlorinated hydrocarbon composition enters the flash distillation pot and is intimately mixed there with the oil. Since the chlorinated hydrocarbon, e.g., a mixture of 1,1-dichloroethane and methylchloroform, is almost immediately flashed from the vessel, only a low concentration of chlorinated hydrocarbon is normally maintained in the pot at any time. The iron is constantly precipitated as a relatively fine, dark-colored powder which can be easily removed in any convenient manner, either periodically or continuously, as described above.

The following examples are given as specific illustrations of the invention. It should be understood, however, that the invention is not limited to the specific details set forth in the examples.

EXAMPLE I

The treating vessel was a dried 250-ml. round-bottom flask equipped with a heating mantle, a magnetic stirrer, and a thermocouple connected to a temperature controller. To the reaction flask was attached a distilling head, condenser, receiver, and an addition funnel for adding the liquid chlorinated hydrocarbon which contained ferric chloride. As shown in Table II below, 100 ml. portions of various hydrocarbon oils were charged to the flask after it had been swept with nitrogen. The specific gravities of these oils varied from 0.740 to 0.882. After the oil had been heated to the indicated temperature, the iron-containing liquid chlorinated hydrocarbon was added at a substantially uniform rate over the period of time shown in the table.

The chlorinated hydrocarbon was predominantly 1,1-dichloroethane together with the amounts of 1,1,1-trichloroethane indicated in Table II. In Run No. 3, a single 550 g portion of chlorinated hydrocarbon was actually used but was continuously recycled about 27 times, with fresh $FeCl_3$ being added to the recycle before introducing to the treating vessel.

After all of the chlorinated hydrocarbon liquid had been added to and flashed off from the hydrocarbon oil, the hot oil was filtered through a sintered glass funnel under slight pressure to remove the solid precipitate. The solids were stirred and washed with hexane or other solvent to remove adsorbed oil, which was subsequently recovered from the hexane. The dried, dark solid was weighed and analyzed. The data of the recovered liquids set out in Table II for Run No. 3 were based on the original chlorinated hydrocarbon charge. The losses of chlorinated hydrocarbon amounted to 0.20% 1,1-dichloroethane and 0.36% 1,1,1-trichloroethane per recycle.

Virtually all of the chlorinated hydrocarbon was recovered without dehydrochlorination or tar formation on a single pass through the flasher. Infrared analysis of the hydrocarbon oils showed no build-up of soluble impurities. The solids in all runs were dry and powdery and not hygroscopic or corrosive. In Run No. 3, where sufficient material was used to ensure accuracy, the weight of solid was 91% of the weight of ferric chloride initially added, and the precipitate consisted largely of ferrous chloride ($FeCl_2$ contains 44% Fe). The precipitate would always weigh 78% of the amount of ferric chloride initially present if the precipitate were only ferrous chloride. The data indicate that the precipitate itself contained, on a weight basis, about 81% $FeCl_2$ and about 19% contaminant such as, carbon, polymer, etc. The total quantity of precipitate requiring disposal is less than the total quantity of $FeCl_3$ catalyst present to the hydrochlorination step and is thus very small.

TABLE II

Flashing of Ferric Chloride-Containing Mixtures of Chlorinated Hydrocarbon Compositions From Various Oils

| Run No. | 1 | 2 | 3 |
|---|---|---|---|
| Hydrocarbon oil | n-Dodecane | USP Mineral Oil (Squibb) | Sontex-55NF (Marathon Morco) |
| Average carbon no. | $C_{12}$ | $C_{29}$ | $C_{22}$ |
| Estimated initial b.p. (°C.) | 214 | 450 | 370 |
| Weight (g) | 75.1 | 88.2 | 82.6 |
| Chlorinated Hydrocarbon | | | |
| Weight (g) | 233 | 277 | 14542 |
| 1,1-Dichloroethane (%) | 84.7 | 84.8 | 84.0 |
| 1,1,1-Trichloroethane (%) | 15.3 | 15.2 | 16.0 |
| Ferric chloride (ppm) | 1320 | 1508 | 688 |
| Oil temperature (°C.) | 110 | 120 | 115 |
| Duration of run (hrs) | 0.75 | 0.9 | 44.8 |
| Recovered liquids (%) | | | |
| Oil | 99.7 | 100 | 100 |
| 1,1-Dichloroethane | 98.8 | 98.7 | 94.6 |
| 1,1,1-Trichloroethane | 97.2 | 99.2 | 90.3 |
| % Oil in distillate | 1.86 | — | 0.01 |
| Recovered solids | | | |
| Dried solids (g) | 0.35 | 0.48 | 9.12 |
| Wt ratio Solids Out/FeCl$_3$ In | 1.13 | 1.50 | 0.91 |
| Analysis of recovered solid | | | |
| Fe (wt %) | — | 21.88 | 34.72 |
| Cl (wt %) | — | — | 46.19 |
| Cl/Fe (molar) | — | — | 2.09 |

EXAMPLE II

A simple rapid screening method for prospective oils was devised which involved the determination of whether ferric chloride would react rapidly with the oil (no chlorinated hydrocarbon present) and form a manageable precipitate. All of the hydrocarbon oils evaluated by this method successfully passed the test. Three of the oils so tested were also employed in separation runs with chlorinated hydrocarbons, as reported in Table I, thereby confirming the validity of the screening method.

The treating vessel was a dried 250-ml, round-bottom flask equipped with a heating mantle, a magnetic stirrer, and a thermocouple connected to a temperature controller. To the reaction flask was attached a vapor take-off to a fluorocarbon bubbler and a water trap for absorbing evolved hydrogen chloride. A nitrogen purge inlet was fitted to the body of the flask. As shown in Tables III and IV below, 100-ml portions of various hydrocarbon oils with or without small amounts of additives were charged to the flask after it had been swept with nitrogen. The specific gravities of the oils varied from 0.740 to 0.882. With the oil still at room temperature, a 10-g portion (40-g in the case of Run Number 1, Table III) of ferric chloride, handled to exclude moisture, was added to the flask. The equipment was sealed and the reactants were heated to the final temperature with stirring over a period of about thirty minutes. The temperature where significant evidence of reaction (gas evolution or color change) began was recorded as the activation temperature.

At the end of the period the system was purged well with nitrogen through the water trap to insure absorbance of all evolved hydrogen chloride. The yield of hydrogen chloride was determined by titration of the trap, and the percentage yield was based on a theoretical yield of one mole per mole of ferric chloride. The solid was collected on a filter, washed with dry hexane, dried and weighed. The oil was recovered, including that from the hexane washings.

The tests in Table III indicate that alkanes and mixtures of alkanes as well as olefins and alkylated aromatics containing an aliphatic moiety of at least six carbon atoms per molecule react rapidly with ferric chloride at low temperatures, in some cases below 30° C. and with many of the preferred oils at between about 30° C. and about 75° or 100° C., and give easily managed precipitates. Tests in Table IV show the reactivity of ferric chloride with partially halogenated and olefinic derivatives of long-chain alkanes even in the presence of large amounts of an alkane. In fact, the ferric chloride sometimes reacts with these derivatives preferentially.

TABLE III

Screening Tests with Various Oils for Reaction with Ferric Chloride

| Run No. | 1 | 2 | 3 | 4 | 5 | 6 | 7 |
|---|---|---|---|---|---|---|---|
| Hydrocarbon oil | n-Dodecane Phillips | USP Min. Oil Squibb | Sontex-55NF Marathon Morco | Soltrol-220 Phillips | Peneteck Penreco | 1-Decene Aldrich | Nalkylene 500 (Conoco) |
| Avg. carbon no. | $C_{12}$ | $C_{29}$ | $C_{20}$ | $C_{14}$ | $C_{15}$ | $C_{10}$ | $C_{18}$ |
| Nature of oil | Alkane | White Min. Oil | White Min. Oil | Branched Alkane | White Min. Oil | Olefin | Dodecylbenzene |
| Est. initial b.p., °C. | 214 | 450 | 370 | 238 | 269 | 172 | — |
| Weight, g | 75.1 | 88.2 | 82.6 | 79.2 | 80.9 | 74.0 | 85.8 |
| Weight FeCl$_3$, g | 40.0 | 10.0 | 10.0 | 10.0 | 10.0 | 10.0 | 10.0 |
| Activation temp.[a] | ca 100 | ca 100 | 35-40 | 50-60 | 72 | 30 | 30-33 |
| Final temp., °C.[b] | 120 | 135 | 125 | 120 | 120 | 100 | 115 |

TABLE III-continued

Screening Tests with Various Oils for Reaction with Ferric Chloride

| Run No. | 1 | 2 | 3 | 4 | 5 | 6 | 7 |
|---|---|---|---|---|---|---|---|
| Time at final temp., hrs | 2.0 | 3.0 | 1.5 | 0.5 | 2.0 | 2.0[c] | 0.25 |
| Yield of HCl, %[d] | 79.6 | 70.9 | 79.9 | 74.9 | 72.5 | 0.0 | 77.9 |
| Recovered oil, % | 96.1 | 96.3 | 98.8 | 94.7 | 98.8 | — | — |
| Recovered solids - | | | | | | | |
| Dried solids, g | 34.29 | 9.0 | 9.04 | 8.8 | 8.11 | 8.23 | 9.01 |
| Wt ratio: Solids out/FeCl$_3$ in | 0.857 | 0.900 | 0.904 | 0.880 | 0.811 | 0.823 | 0.901 |
| Analysis of recovered solid | | | | | | | |
| Fe, wt % | 42.55 | 34.30 | 39.14 | 37.56 | 37.12 | 41.63 | — |
| Cl, wt % | 50.22 | 47.10 | 48.67 | 48.11 | 48.47 | 51.19 | — |
| Cl/Fe molar ratio | 1.86 | 2.16 | 1.96 | 2.02 | 2.06 | 1.94 | — |
| Total mass accountability, % | 98.7 | 97.3 | 99.8 | 95.9 | 98.6 | 99.3 | — |

[a]Temperature where vigorous reaction began
[b]Evidence of reaction had usually ceased by the time this temperature was reached.
[c]Although no HCl was evolved, a color change occurred which was complete by final temperature.
[d]Yield of HCl based on a theoretical maximum of one of HCl per mole of ferric chloride.

TABLE IV

Screening Tests For Reaction of Ferric Chloride with Olefins and Chlorinated Hydrocarbons in Dodecane

| Run no. | 1 | 2 |
|---|---|---|
| Hydrocarbon oil | n-Dodecane (75.1g) | n-Dodecane (75.1g) |
| Additives | 2% Decene-1 | 1.2% 2-chloroocatane 0.8% Octenes |
| Wt FeCl$_3$, g | 10.0 | 10.0 |
| Final Temp., °C. | 125 | 100 |
| Time at final temp. (hrs) | 0.5 | 2.3 |
| Yield of HCl, %[a] | 82.0 | 82.1 |
| Recovered oil, %[b] | | |
| Dodecane | 99.1 | 99.3 |
| Decene-1 | 6.3 | — |
| 2-Chlorooctane | — | 8.3 |
| Octenes | — | 27.2 |
| Recovered solids | | |
| Dried solids, g | 8.87 | 9.13 |
| Wt ratio Solids out/FeCl$_3$ in | 0.887 | 0.913 |
| Total mass accountability, % | 98.4 | 99.1 |

[a]Yield of HCl based on a theroretical maximum of one mole of HCl per mole of ferric chloride.
[b]Recovery of each component is stated as a percentage of the original amount present.

It is to be understood that the foregoing detailed description is given merely by way of illustration and that many variations may be made therein without departing from the spirit or scope of the invention claimed below.

What we claim is:

1. A process for the removal of ferric chloride from chlorinated aliphatic hydrocarbons having less than 6 carbon atoms per molecule, comprising the steps of:
   (a) mixing a liquid comprising a major amount of at least one relatively volatile chlorinated aliphatic hydrocarbon having less than 6 carbon atoms per molecule and 0.01% to 3% ferric chloride admixed therewith, with at least 10 volumes (per 100 volumes of volatile chlorinated hydrocarbon) of a relatively less volatile oil composition comprising at least one hydrocarbon having at least 6 carbon atoms per molecule and selected from the group consisting of alkanes, cycloalkanes, alkenes, cycloalkenes, alkyl aromatic hydrocarbons containing at least 6 carbon atoms per alkyl group, and mixtures of at least two of the foregoing;
   (b) heating the resulting mixture at a temperature between 60° and about 140° C. until at least 95% of the ferric iron present is reduced to the divalent state and an easily filtrable, essentially inert, non-hazardous, powdery solid precipitate consisting largely of ferrous chloride combined with a small amount of carbonaceous material is formed without significant decomposition of said chlorinated hydrocarbon;
   (c) separating said chlorinated hydrocarbon as a vapor from said oil composition and from said precipitate;
   (d) mechanically separating said precipitate from said oil composition;
   (e) washing adsorbed oil from said separated precipitate with relatively volatile liquid chlorinated hydrocarbon which has been recovered from the process; and
   (f) recycling the resulting oil-containing chlorinated hydrocarbon to contacting step (a).

2. A process for the removal of ferric chloride catalyst from a liquid composition comprising a relatively volatile chlorinated saturated aliphatic hydrocarbon containing 2 to 5 carbon atoms and 2 to 3 chlorine atoms per molecule, comprising the steps of:
   (a) continuously adding in a flash zone a relatively volatile chlorinated hydrocarbon liquid containing 0.01 to 3% ferric chloride catalyst admixed therewith resulting from the catalytic hydrochlorination of a member of the group consisting of ethylene, propylene, vinyl chloride, vinylidene chloride and mixtures thereof, to a body containing at least 10 volumes (per 100 volumes of said volatile chlorinated hydrocarbon) of a relatively less volatile oil comprising at least one hydrocarbon having at least an average of 12 carbon atoms per molecule and composed of predominantly aliphatic hydrocarbons having a boiling range at least predominantly above about 180° C., and maintaining said body at a temperature in the range between 60° and 140° C. and which is substantially below the boiling range of said oil and above the boiling point of said relatively volatile chlorinated hydrocarbon liquid whereby the latter is flashed off and until at least 60% of the ferric iron present is converted to the divalent state and an easily filtrable, essentially inert, powdery, non-hazardous precipitate consisting largely of ferrous chloride combined with a small amount of carbonaceous material is formed in said oil by interaction of said ferric chloride with said oil;
   (b) removing said chlorinated hydrocarbon from said zone in a vapor form and recovering the same, leaving behind a mixture of oil and said precipitate;
   (c) mechanically separating said mixture into said solid precipitate and a liquid oil franction; and
   (d) washing adsorbed oil from said separated precipitate with chlorinated hydrocarbon recovered from step (b) and thereafter recycling the resulting wash liquid to said flash zone.

* * * * *